(12) United States Patent
McLean et al.

(10) Patent No.: US 9,953,140 B2
(45) Date of Patent: Apr. 24, 2018

(54) SYSTEMS, METHODS, AND APPARATUSES FOR SECURELY DISPENSING ONE OR MORE PRESCRIBED SUBSTANCES TO A SECURELY IDENTIFIED INTENDED USER

(71) Applicant: PillTek LLC, Atlanta, GA (US)

(72) Inventors: Martin Lord McLean, Pelham, MA (US); Larry Van Thomas Crisco, Jacksonville, FL (US); Ashley Brian Hancock, Atlanta, GA (US); Patrick William Strane, Atlanta, GA (US); Mark Patrick McJunkin, Peachtree City, GA (US)

(73) Assignee: INTENT SOLUTIONS, INC., Atlanta, GA (US)

( * ) Notice: Subject to any disclaimer, the term of this patent is extended or adjusted under 35 U.S.C. 154(b) by 376 days.

(21) Appl. No.: 14/215,837

(22) Filed: Mar. 17, 2014

(65) Prior Publication Data
US 2014/0278510 A1 Sep. 18, 2014

Related U.S. Application Data

(60) Provisional application No. 61/788,492, filed on Mar. 15, 2013.

(51) Int. Cl.
*G06F 19/00* (2018.01)
*A61J 7/00* (2006.01)
(Continued)

(52) U.S. Cl.
CPC ........ *G06F 19/3462* (2013.01); *A61J 7/0076* (2013.01); *A61J 7/04* (2013.01);
(Continued)

(58) Field of Classification Search
CPC ......... G06F 17/00; G07F 11/00; B65B 59/00; A61J 7/02; A61J 7/0481
(Continued)

(56) References Cited

U.S. PATENT DOCUMENTS 4,572,403 A 2/1986 Benayora
4,785,969 A 11/1988 McLaughlin
(Continued)

FOREIGN PATENT DOCUMENTS

CA 1258832 8/1989
CA 2152785 1/1994
(Continued)

OTHER PUBLICATIONS

"Facts on NASPER"; ASIPP, 2010.*
(Continued)

*Primary Examiner* — John A Pauls
(74) *Attorney, Agent, or Firm* — Eversheds Sutherland (US) LLP

(57) ABSTRACT

Systems, methods, and apparatuses for securely dispensing one or more prescribed substances at a given time and/or date are disclosed herein. In certain embodiments, a pill dispensing device may include a generally tamper-proof portable housing. A replaceable cartridge may be configured to be removably disposed within the portable housing. The replaceable cartridge also may be generally tamper-proof. The portable housing and/or the replaceable cartridge may be operable to dispense a predefined amount of a prescribed substance at a given time and/or date.

19 Claims, 10 Drawing Sheets

(51) Int. Cl.
*A61J 7/04* (2006.01)
*A61J 7/02* (2006.01)

(52) U.S. Cl.
CPC ............ *A61J 7/02* (2013.01); *A61J 7/0436* (2015.05); *A61J 7/0445* (2015.05); *A61J 2200/30* (2013.01); *A61J 2200/70* (2013.01)

(58) Field of Classification Search
USPC ............ 206/528; 700/237, 242; 455/41.1; 340/540
See application file for complete search history.

(56) References Cited

U.S. PATENT DOCUMENTS

| | | | |
|---|---|---|---|
| 4,911,327 | A | 3/1990 | Shepherd et al. |
| 5,522,525 | A | 6/1996 | McLaughlin et al. |
| 6,216,910 | B1 | 4/2001 | Numerick |
| 6,324,123 | B1 | 11/2001 | Durso |
| 6,601,729 | B1 * | 8/2003 | Papp ............ A61J 7/0084 206/528 |
| 6,611,733 | B1 | 8/2003 | De La Huerga |
| 6,625,518 | B2 | 9/2003 | Depeursinge |
| 6,705,487 | B2 | 3/2004 | Kim |
| 6,732,884 | B2 | 5/2004 | Topliffe et al. |
| 6,766,219 | B1 | 7/2004 | Hasey |
| 6,865,444 | B2 | 3/2005 | Howard |
| 7,108,153 | B2 | 9/2006 | Wood |
| 7,137,528 | B1 | 11/2006 | Yates et al. |
| 7,170,823 | B2 | 1/2007 | Fabricius et al. |
| 7,359,765 | B2 | 4/2008 | Varvarelis et al. |
| 7,440,817 | B2 | 10/2008 | Fu |
| 7,715,277 | B2 | 5/2010 | de la Huerga |
| 7,747,347 | B2 | 6/2010 | Park, IV |
| 7,944,342 | B2 | 5/2011 | Sekura |
| 7,963,201 | B2 | 6/2011 | Willoughby et al. |
| 7,978,564 | B2 | 7/2011 | De La Huerga |
| 8,027,748 | B2 | 9/2011 | Handfield et al. |
| 8,135,497 | B2 | 3/2012 | Joslyn |
| 8,362,914 | B2 | 1/2013 | Hyde et al. |
| 8,636,172 | B2 | 1/2014 | Dunn |
| 2004/0122554 | A1 * | 6/2004 | Howard ............ A61F 13/551 700/237 |
| 2004/0129716 | A1 | 7/2004 | Naufel et al. |
| 2006/0071011 | A1 * | 4/2006 | Varvarelis ............ A61J 7/0481 221/9 |
| 2006/0157491 | A1 | 7/2006 | Whittle et al. |
| 2008/0027579 | A1 * | 1/2008 | van der Hoop ........ A61J 7/0076 700/242 |
| 2008/0251530 | A1 | 10/2008 | Holloway et al. |
| 2008/0300719 | A1 * | 12/2008 | Duke ............ A61J 7/0481 700/244 |
| 2009/0105876 | A1 * | 4/2009 | Simpson ............ A61J 7/0084 700/242 |
| 2009/0218363 | A1 * | 9/2009 | Terzini ............ A61J 7/02 221/4 |
| 2009/0223994 | A1 | 9/2009 | Getz |
| 2010/0318218 | A1 | 12/2010 | Muncy, Jr. et al. |
| 2011/0270442 | A1 | 11/2011 | Conley et al. |
| 2012/0003928 | A1 * | 1/2012 | Geboers ............ A61J 7/0084 455/41.1 |
| 2013/0187774 | A1 * | 7/2013 | Muecke ............ G07C 9/00126 340/540 |

FOREIGN PATENT DOCUMENTS

| | | |
|---|---|---|
| CA | 2130252 | 2/1996 |
| CA | 2217220 | 6/1998 |
| CA | 2605237 | 9/2006 |
| WO | 02/17850 A1 | 3/2002 |
| WO | 2012148976 | 1/2012 |

OTHER PUBLICATIONS

International Search Report and Written Opinion for International Application No. PCT/US2014/030211 dated Jul. 15, 2014.

* cited by examiner

SYSTEMS, METHODS, AND APPARATUSES FOR SECURELY DISPENSING ONE OR MORE PRESCRIBED SUBSTANCES TO A SECURELY IDENTIFIED INTENDED USER

CROSS-REFERENCE TO RELATED APPLICATION

The disclosure claims priority to and the benefit of U.S. provisional application No. 61/788,492, filed Mar. 15, 2013, which is hereby incorporated by reference in its entirety.

FIELD

The disclosure generally relates to medication dispensing devices and more particularly relates to systems, methods, and apparatuses for dispensing one or more medication substances to a securely identified intended user.

BACKGROUND

Unintended use of prescription medications by the intended user or others is a serious problem. The misuse of legitimately prescribed medications such as painkillers, stimulants, tranquilizers, sedatives, and steroids kills tens of thousands of Americans and costs the U.S. healthcare system more than $100 billion a year. The biggest impact is from opiate painkillers, but deaths and injuries are often caused by simultaneous exposure to multiple classes of Controlled Substances and drugs of potential abuse. Opiates remain the medications of choice to treat legitimate acute and chronic pain. In the U.S. alone, 130 million prescriptions were written in 2010 for hydrocodone, which has become a widespread source of abuse and drug trafficking. All told, approximately 500 million Controlled Substance prescriptions are written in the U.S. each year. According to recent congressional data, prescription drug abuse is the leading cause of accidental death in the U.S., now exceeding traffic accidents, and also exceeding deaths from heroin and cocaine, combined. Approximately 60% of prescribed medication is not taken as directed.

In 2010, over 38,000 unintentional drug overdose deaths occurred in the United States, 60% of those involving prescription medications. Prescription drug abuse is the fastest growing drug problem in the United States. The increase in unintentional drug overdose death rates in recent years has been driven by increased use of a class of prescription opioid analgesics. In addition, recent data suggests that for every unintentional overdose death related to an opioid analgesic, 10 persons are admitted for substance abuse treatment, 32 visit emergency departments, 130 report drug abuse or dependence, and 825 report nonmedical uses of opioid analgesics. Prescription drugs are the second-most abused category of drugs after marijuana.

Medications, such as opioid analgesics and narcotics, may be prone to abuse or diversion, for instance taken in excess or diverted and sold to others who would abuse the medication. The two main populations in the United States at risk for prescription drug overdose are the approximately 9 million persons who report long-term medical use of opioids and the roughly 12 million persons who report non-medical use (i.e., use without a prescription or medical need) annually. In an attempt to treat patient pain better, practitioners have greatly increased their rate of opioid prescribing over the past decade. Persons who abuse opioids have learned to exploit this new practitioner sensitivity to patient pain, and clinicians struggle to treat patients without overprescribing these drugs. The regulatory response to inform the prescriber about the potential abusers recent prescription history through an updated electronic health record is currently part of the attempt to address one aspect of this problem. This, however, still does not address the availability of the entire contents of a legitimately prescribed opioid capped bottle to anyone once it's opened, in any amount, at any frequency. The chain of command for the drug of potential abuse is lost once it leaves the pharmacy.

It is desirable to prevent the misuse of medications by intended users and also to ensure correct dispensing of prescription medications. It would be useful to provide a low-cost portable dispenser and monitoring system to verify that medications stored therein are not taken in excess (i.e., abused) and are only taken at the prescribed interval and dose. It also would be useful to provide a portable dispenser and monitoring system to verify that medications stored therein are removed only by the patient or another authorized person in order to prevent drug abuse and diversion.

SUMMARY

Some or all of the foregoing needs and/or problems may be addressed with one or more of the embodiments of the present disclosure. In certain embodiments, the systems, methods, and apparatuses for securely dispensing one or more prescribed substances (i.e., a prescribed drug) at a given time and/or date or on demand to a securely identified intended user may include a generally tamper-proof portable housing. In some instances, a replaceable cartridge or the like may be configured to be removably disposed within the portable housing. In other instances, the cartridge may be omitted. The cartridge also may be generally tamper-proof. The cartridge and/or the portable housing may be operable to dispense a predefined amount of a prescribed substance at a given time and/or date or on demand to a securely identified intended user. The cartridge may be operable to store information associated with a prescribed substance and/or a patient. The apparatus may be loaded with one or more prescription medications by a pharmacist or other trained persons at a pharmacy interaction or at a mail-order pharmacy. The apparatus may include encrypted secure identifiable information connecting the intended user to the apparatus, the contents, and/or the dispensing dose, frequency and/or duration. That is, the apparatus may be configured to only dispense to the intended user upon secure identification thereof and will not dispense to others. Examples of identity strategies may include, but are not limited to, fingerprint identification, pin code encryption, face-recognition, multi-source identification software, and the like. Any identification means may be used herein.

The device may interact with a medication and information loading device or docking station at the pharmacy counter or elsewhere, into which the pharmacist or the patient may load the prescribed medication, and also into which the dispensing apparatus is inserted to receive the medication. This loading system may include identification encryption methods to contemporaneously securely connect the contents to the identified user. Alternatively, the apparatus may be loaded with a cartridge that contains medication previously loaded by the pharmacist. The cartridge may also be inserted into a loading system or docking station at the pharmacy counter or elsewhere, into which the dispensing apparatus also may be inserted to receive the cartridge. This loading system may include identification encryption methods to contemporaneously securely connect the cartridge and contents to the identified user.

Other features and aspects of the disclosure will be apparent or will become apparent to one with skill in the art upon examination of the following figures and the detailed description. All other features and aspects, as well as other system, method, and assembly embodiments, are intended to be included within the description and are intended to be within the scope of the accompanying claims.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
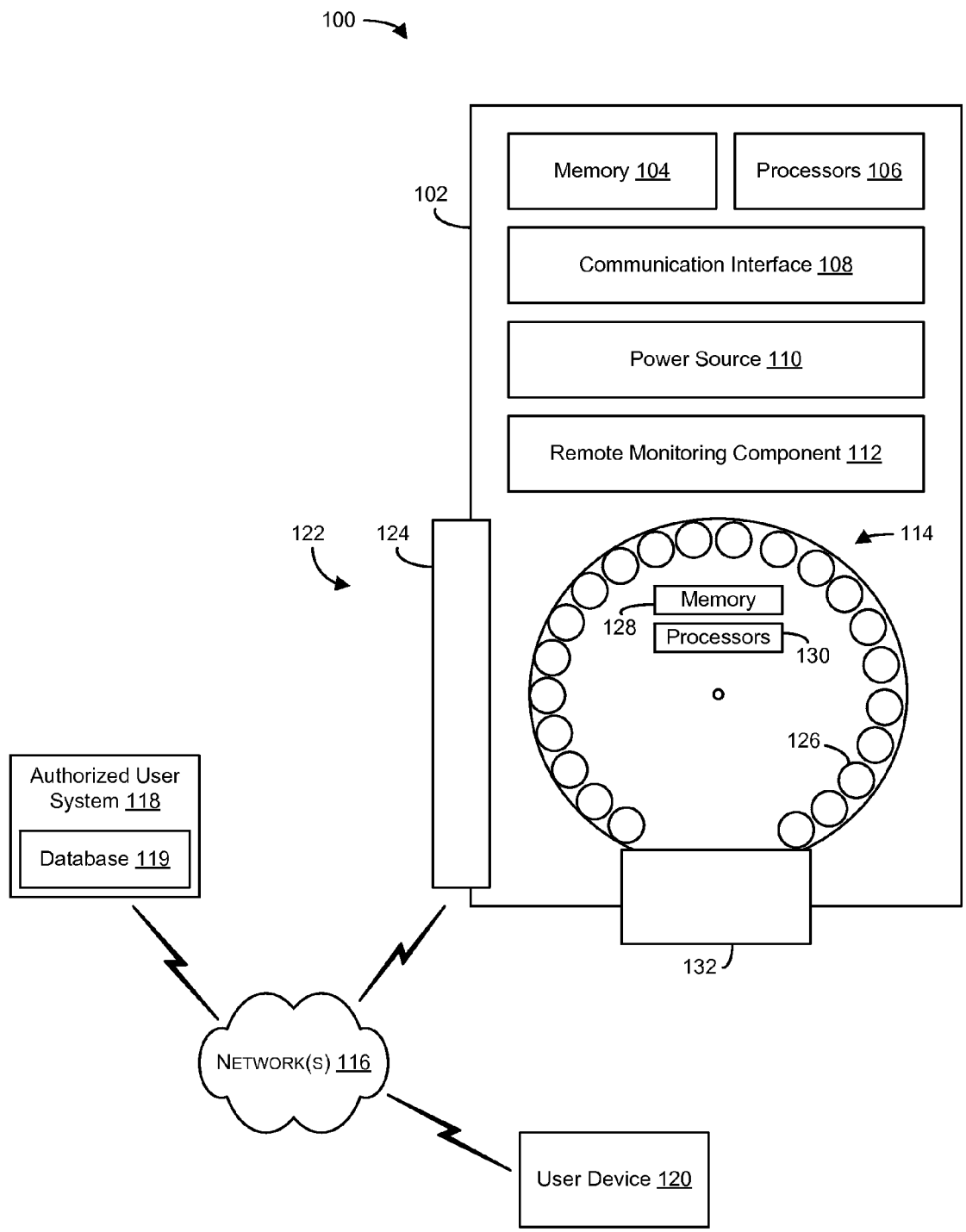
FIG. 1 schematically depicts an example system and apparatus for securely dispensing one or more prescribed substances at a given time and/or date in accordance with one or more embodiments of the disclosure.

Described below are embodiments of systems, methods, and apparatuses for securely dispensing one or more prescribed substances (e.g., a plurality of tablets, pills, or capsules) at a given time and/or date to a securely identified intended user and/or in accordance with a prescribed dosage schedule. Such embodiments may protect the prescribed substance within a portable housing that is generally tamper-proof and may only be opened by authorized personnel, such as a physician, a pharmacist, or a securely identified intended user. In addition, certain embodiments may include a replaceable cartridge (such as a cartridge, magazine, container, bottle, etc.) with one or more segments to hold predefined amounts of the prescribed substance. The replaceable cartridge may be inserted into the portable housing. The cartridge may be operable to store information associated with a prescribed substance and/or a patient, wherein the information can be read or otherwise obtained when needed by the portable housing. Moreover, the replaceable cartridge may be generally tamper-proof and only accessible by authorized personnel. Furthermore, certain embodiments may include a loading device operable to receive a replaceable cartridge and/or the apparatus itself for loading of medications and identity encryption. The loading device also may be operable to communicate information associated with a prescribed substance and/or a patient. Moreover, the loading device may be operable to insert a prescribed substance into the replaceable cartridge and/or the apparatus, depending on the embodiment.

In some instances, the prescribed substance may be an opioid drug or other medications of potential abuse or the like, for which it is desirable to prevent abuse, misuse, or diversion to others than the prescribed patient. The prescribed substance, however, may be any drug, medication, prescription, and/or treatment. For example, the prescribed substance may include one or more solid drug units, such as tablets, capsules, and/or pills. The apparatus may dispense one or more different types of medications. In one example, stimulants, sleep medications, de-tox medications, suboxone, benzodiazepines, and/or anti-anxiety medications may be used herein.

In certain embodiments, the apparatus may include a pill dispensing system for securely dispensing one or more prescribed substances at a given time and/or date to a securely identified intended user. In one example, the pill dispensing system may dispense a range of substances at a range of time intervals, such as, e.g., 1-2 tablets every 4-6 hours. Other dispensing ranges and timetables are possible and are within the scope of the disclosure.

The pill dispensing system may include a portable housing, a replaceable cartridge, a processor, a memory, a power source, and/or a communication interface, although some components may be omitted and others may be added. In some instances, the pill dispensing device may comprise a spring loaded dispenser that is configured to dispense medication. The portable housing may protect the intended medication, the replaceable cartridge, the processor, the memory, the power source, and/or the communication interface from tamper attempts. In some instances, the portable housing may be sized and shaped to be carried by a patient. For example, the portable housing may be configured to be held in the hand of the patient or carried in the pocket of the patient. In this manner, the power source may include at least one battery or the like.

The portable housing may include an opening for inserting and/or removing the replaceable cartridge and/or the medication therein. The opening may be generally tamper-proof and only accessible by authorized personnel. In this manner, only authorized personnel may insert and/or remove the replaceable cartridge and/or the medication to and from the portable housing. For example, the opening may include a locking mechanism or the like. In some instances, the locking mechanism may be a mechanical lock, a biometric lock, an electronic lock, or a combination thereof. For example, a person authorized to insert and/or remove the medication and/or replaceable cartridge, such as a physician, a pharmacist, or to a securely identified intended user, may be required to enter a code, provide a finger print, and/or use a key to access the opening to remove or insert the replaceable cartridge and/or the medication.

Similarly, a person authorized to accept or be the recipient of the dispensed medication contents, such as the intended patient or authorized user, may be required to enter a code, provide a finger print, utilize other forms or encrypted identification, and/or use a key to be dispensed the intended medication at the intended dose, frequency, and/or quantity prescribed. Moreover, the locking mechanism may be voice or otherwise activated. Other locking mechanisms may also be used to prevent tampering with the medication or apparatus. The apparatus may contain notification systems to alert the operating system directly or indirectly to tamper attempts or apparatus destruction.

The replaceable cartridge and/or apparatus may be operable to dispense a predefined amount of a prescribed substance at a given time and/or date to a securely identified intended user. For example, the replaceable cartridge may cooperate with the portable housing to enable an authorized patient to access a predefined amount of a prescribed substance, i.e., the prescribed dose of the prescribed drug at a given time and/or date. In other instances, the apparatus (independent of a cartridge system) may perform the same function. In certain embodiments, the replaceable cartridge (or the apparatus independent of the cartridge system) may hold predefined amounts of prescribed substances and may be configured to accept, quantify, collate and/or dispense the intended medication to a securely identified intended user. The dispensing of the medication may be at the verified user's discretion, limited to a dosage schedule, or a combination thereof.

In other embodiments, the replaceable cartridge may be an elongated member or a wheel-shaped member. In one example, the replaceable cartridge may be a replaceable cartridge with one or more prescribed substances within respective compartments. For example, the replaceable cartridge may have a cassette-like configuration. In some instances, the replaceable cartridge may comprise a medication bottle or the like that is typically used by pharmacists.

The replaceable cartridge may be generally tamper-proof and only accessible by authorized personnel or a securely identified intended user. Further, the apparatus (independent of the cartridge system) may perform the same functions once loaded by a pharmacist or other qualified persons. That is, the systems and methods described herein may be performed by the apparatus and a corresponding insertable cartridge, or alternatively, the systems and methods described herein may be performed by an apparatus that does not include a cartridge. That is, the apparatus itself houses and dispense the medications to a securely identified intended user without the use of a replaceable cartridge.

In certain embodiments, the portable housing and/or the replaceable cartridge may include at least one processor in communication with at least one memory. The processor and/or memory may include computer-executable instructions to operate the power source to manipulate the replaceable cartridge at the given time and/or date. Further, the communication interface may be operable to receive instructions to operate the power source to manipulate the replaceable cartridge at the given time and/or date or at the verified user's discretion. In this manner, based at least in part on the computer-executable instructions and/or the communication interface, the replaceable cartridge and/or the portable housing may be manipulated to enable a securely identified intended user to access a predefined amount of a prescribed substance at a given time and/or date. For example, the replaceable cartridge may provide a predefined amount of a prescribed substance to an access port within the portable housing that is accessible by the securely identified intended user. In some instances, the securely identified intended user may request that the portable housing and/or the replaceable cartridge dispense the prescribed substance on demand. In such instances, the portable housing and/or the replaceable cartridge may be configured to monitor how much drug is being dispensed over time, and in some instances, may limit the dispensing of the drug if it is being abused.

In some instances, the patient may be required to provide verification in order to access the prescribed substance. For example, the patient may be required to enter a code, provide a finger print, utilize other forms or encrypted identification, and/or use a key to gain entry to the access port within the portable housing in order to access the prescribed substance. Any biometric identifier may be used to prevent unauthorized access to the prescribed substance by someone other than the patient. For example, in some instances, voice or face recognition software may be used to verify the patient's identity. Other access controls may also be used to prevent unauthorized access to the prescribed substance including, but not limited to, pin-code security or the like.

In some instances, the pill dispensing system may include a remote monitoring component, which may receive an indication when the portable housing, the replaceable cartridge, and/or the intended medication is compromised. In addition, in certain embodiments, the remote monitoring component may be configured to receive an indication to dispense a prescribed substance at a time and/or date other than a programmed time and/or date. An alert may be generated and transmitted by the processor and/or the remote monitoring component if the prescribed substance is dispensed at a time and/or date other than a programmed time and/or date, or if the portable housing and/or the replaceable cartridge is compromised or opened, or if someone other than the patient accesses or attempts to access the prescribed substance.

In certain embodiments, the remote monitoring component may be configured to monitor the on demand dispensing of medication to determine if the medication is being abused. If it is determined that the medication is being abused, the remote monitoring component send a signal to limit the dispensing of the medication or stop the dispensing of the medication altogether.

In one example, if the portable housing and/or replaceable cartridge is compromised or otherwise dispenses a prescribed substance at a time and/or date other than a programmed time and/or date, the prescribed substance may be rendered inert by the addition or release of a counter substance that may react with the prescribed substance to render it inert.

Other embodiments may include a time-limited device connection with a support system by direct interaction through, for example, a USB connect or the like to confirm apparatus function and the absence of a failed use or tamper attempt at pre-defined intervals (e.g., daily or every other day, etc.). Such a connection may be required for the apparatus to function properly. In other instances, the pill dispensing system may communication over a network (e.g., wireless, cellular, etc.) or the like.

In certain embodiments, authorized personnel, such as a physician or a pharmacist, may insert the replaceable cartridge (e.g., a pill bottle or the like) into the portable housing. In some instances, the replaceable cartridge may be readymade. That is, the replaceable cartridge may be prefilled with prescribed substances from the manufacturer. In other instances, the authorized personnel, e.g., a pharmacist, may prepare the replaceable cartridge for insertion into the portable housing. That is, the authorized personnel may provide a predefined amount of prescribed substance in the compartments of the replaceable cartridge. In certain embodiments, the authorized personnel may program the processor and/or memory associated with the replaceable cartridge to communicate with the portable housing to provide the patient with a predefined amount of a prescribed substance at a given time and/or date. For example, the replaceable cartridge may provide a predefined amount of a prescribed substance to an access port within the housing that is accessible by the patient at the given time and/or date based on the instructions provided by the authorized personnel.

In other embodiments, authorized personnel, such as a physician or a pharmacist, may insert the prescribed substances directly into the portable housing. This is, in this embodiment, the cartridge may be omitted and the portable housing itself may include all of the functionality described herein. For example, the authorized personnel may provide a predefined amount of prescribed substance in the portable housing. In certain embodiments, the authorized personnel may program the processor and/or memory associated with the portable housing to provide the patient with a predefined amount of a prescribed substance at a given time and/or date. In other instances, the verified user may dispense the medication at will. In some instances, the patient may be required to provide identification information in order to obtain the prescribed substance.

In some embodiments, a loading device may be provided to receive a replaceable cartridge and to insert a prescribed substance into the replaceable cartridge. In other instances, the loading device may receive the apparatus, such as the portable housing. The loading device may be operated by a pharmacist or other personnel responsible for distributing a prescribed substance or otherwise loading the replaceable cartridge and/or the portable housing with the prescribed substance. The loading device may include a reader and/or programming device to facilitate communication with the replaceable cartridge and/or the portable housing. The loading device (or docking station) may be located at a pharmacy counter or elsewhere. The pharmacist or the patient may insert the prescribed medication into the loading device. Moreover, the pharmacist or the patient may insert the cartridge and/or dispensing apparatus into the loading device to receive the medication. The loading device may then load the dispensing apparatus with medication. The loading device may include identification encryption functionality to contemporaneously securely associate the contents to the identified user. Alternatively, the apparatus may be loaded with a cartridge that contains medication previously loaded by the pharmacist.

In certain instances, when a paper and/or electronic prescription is received, prescription information and/or patient information may be transmitted or otherwise input to the loading device. The loading device may transmit some or all of the prescription information and/or patient information to a replaceable cartridge or the portable housing when the replaceable cartridge or the portable housing is in communication with the loading device. Prescription information may include a name of a prescribed substance, a dosage regimen, a patient's contact information, a prescriber's contact information, a pain scale, etc.

As noted above, in some embodiments, the apparatus may not contain a cartridge. In this manner, the apparatus may be inserted into a loading or docking station, which temporarily engages the apparatus for medication loading, identity encryption for the intended user, encryption of contents, and prescriptive information. The loading device may be accessed on one side by the pharmacist (or other qualified persons) for medication loading and by the intended user on the other side. That is, the intended user may insert the apparatus on one side of the loading device and the pharmacist may load medication on the other side of the loading device. In this manner, the loading device may be located, for example, on the pharmacy counter or other location such as a doctor's office or dispensary. This configuration may ensure that the patient does not have unauthorized access to the medication.

Although the systems and methods described herein are discussed in relation to controlled substances, any material, substance, article, etc., (e.g., precious metals, jewels, or the like) may be used herein. That is, the systems and methods described herein may be used in conjunction with the secure transfer of any high value substance or the like. For example, the systems and methods described herein may be used to securely transport and dispense small unit, high-value objects, such as jewels, gemstones, microelectronics, or anything else.

These and other embodiments of the disclosure will be described in more detail through reference to the accompanying drawings in the detailed description of the disclosure that follows. This brief introduction, including section titles and corresponding summaries, is provided for the reader's convenience and is not intended to limit the scope of the claims or the proceeding sections. Furthermore, the techniques described above and below may be implemented in a number of ways and in a number of contexts. Several example implementations and contexts are provided with reference to the following figures, as described below in more detail. However, the following implementations and contexts are but a few of many.

Illustrative Embodiments

FIG. 1 schematically depict a pill dispensing device 100 for securely dispensing one or more prescribed substances at a given time and/or date to a securely identified intended user. The pill dispensing device 100 may be configured to protect the prescribed substance within a portable housing 102 that is generally tamper-proof and may only be opened for medication loading by authorized personnel, such as a physician, a pharmacist, or a securely identified intended user. In some instances, the portable housing 102 may be sized and shaped to be carried by a patient. For example, the portable housing 102 may be configured to be held in the hand of the patient and/or carried in the pocket of the patient. In one example embodiment, the housing is from about 3 inches to about 8 inches long, from about 2 inches to about 6 inches wide, and from about 0.25 inches to about 1.5 inches thick. Other dimensions are within the scope of the disclosure.

In certain embodiments, the portable housing 102 may include a memory 104, a processor 106, a communication interface 108, a power source 110 (e.g., a battery), and/or a remote monitoring component 112. Moreover, in some instances, the pill dispensing device 100 may include a replaceable cartridge 114 configured to be inserted and/or removed from the portable housing 102, although in other embodiments the cartridge 114 may be omitted. The portable housing 102 may protect the memory 104, the processor 106, the communication interface 108, the power source 110, the remote monitoring component 112, the prescribed substance, and/or the replaceable cartridge 114 from tamper attempts.

In some instances, the communication interface 108 may comprise a graphical user interface or the like. The communication interface 108 may enable a user to interact with the pill dispensing device 100 to control, dispense, monitor, communicate with, and/or observe the various aspects of the device. For example, the communication interface 108 may be operable to receive instructions to operate the power source 110 to manipulate the replaceable cartridge 114 at a given time and/or date to securely dispense one or more prescribed substances to a securely identified intended user. In some instances, the communication interface 108 may be operable to receive instructions from the securely identified intended user to dispense one or more prescribed substances on demand.

In addition, the communication interface 108 may provide alerts and/or reminders to the user, such as a green light indicating that a pill has been dispensed or can be dispensed if needed, a yellow light to indicate an approaching dispensing interval, and a red light to indicate the absence of accessibility. Moreover, the communication interface may include verbal commands, haptic feedback, and/or written commands. Other alerts and/or reminders may be used. In some instances, the communication interface 108 may include a monitor and/or controls. Further, the communication interface 108 may be configured to receive input from a user of the pill dispensing device 100. For example, the user may provide an indication that a pill has been taken, or the user may request pills.

The communication interface 108 may include functionality to verify the patient's identity. That is, the patient may be required to provide verification in order to access the prescribed substance within the pill dispensing device 100. For example, the patient may be required to enter a code, provide a finger print, provide face or voice recognition, activate an identity sequence or verify themselves through an attached handheld phone or computer, and/or use a key to gain entry to an access port 132 within the portable housing 102 in order to access the prescribed substance. Any biometric identifier may be used to prevent unauthorized access to the prescribed substance. For example, in some instances, voice or face recognition software may be used to verify the patient's identity. In this manner, the communication interface 108 may include a camera, touch screen, receiver, microphone, etc. Other access controls may also be used to prevent unauthorized access to the prescribed substance. In this manner, only securely identified intended users may have access to the medication.

In certain embodiments, the remote monitoring component 112 may include wireless functionality to facilitate wireless communication with one or more devices over a network 116. For example, the pill dispensing device 100 may be in communication with an authorized user system 118 (e.g., a pharmacy or hospital) over the network 116. The authorized user system 118 may include a database 119 that includes information associated with the pill dispensing device 100, such as medication type, dosage, patient information, prescriber information, pain scale etc. In this manner, an operator of the authorized user system 118 may remotely communicate with, transmit to, receive from, monitor, and/or control various aspects of the pill dispensing device 100.

In one example, the authorized user system 118 may increase or decrease dosage based on the patient's condition, such as an increased pain level or improved condition. In another example, the authorized user system 118 may receive an alert if the prescribed substance is dispensed at a time and/or date other than a programmed time and/or date, or if the portable housing 102 and/or replaceable cartridge 114 are compromised or opened. In yet another example, the authorized user system 118 may receive a report (hourly, daily, weekly, etc.) regarding medication usage. Moreover, the authorized user system 118 may remotely alter the medication schedule of the pill dispensing device 100. In some instances, the authorized user system 118 may monitor the dispending of medication to determine if the medication is being abused. In such instances, the authorized user system 118 may limit or prevent the dispensing of medication.

In certain embodiments, interaction of the pill dispensing device 100 with the network 116 may be direct through a physical connection or indirect via a wireless network. In one example, in the event of a medicine recall and/or if the medication has expired, the pill dispensing device 100 can be locked and/or the patient may be notified. Moreover, the pill dispensing device 100 may include a GPS module or the like. In this manner, the location of the pill dispensing device 100 may be monitored, or if the pill dispensing device 100 is lost or stolen, it may be tracked down.

In some instances, the pill dispensing device 100 may be in direct or indirect communication with a user device 120 (e.g., a cell phone, laptop, tablet, and/or a mobile application thereon, etc.) over the network 116. In this manner, the user device 120 may remotely communicate with, transmit to, receive from, monitor, and/or control the various aspects of the pill dispensing device 100 described herein. For example, alerts may be transmitted to the user device 120 to remind the patient to take a pill and/or provide the patient with medication instructions. In addition, the patient may be required to enter a code, answer a question, activate an identity encryption sequence, use face or any form of biometric recognition, and/or speak into the user device 120 in order to receive a dosage of the prescribed substance from the pill dispensing device 100. In some instances, the user device 120 may be required to be within a certain proximity of the pill dispensing device 100 in order for the pill dispensing device 100 to dispense medication. That is, the user device 120 (such as a cell phone or the like) may be associated with an intended patient. In other instances, the user device 120 may generate, transmit, and/or receive reports regarding adherence, attempts to access medications, amount of medication dispensed, symptom levels, recall information etc.

The portable housing 102 may include an opening 122 for inserting and/or removing the replaceable cartridge 114 and/or the medication therein. The opening 122 may be generally tamper-proof and only accessible by authorized personnel and/or a securely identified intended user. In this manner, only authorized personnel may insert and/or remove the replaceable cartridge 114 and/or medication into the portable housing 102. For example, the opening 122 may include a locking mechanism 124 or the like. In some instances, the locking mechanism 124 may be a mechanical lock, a biometric lock, an electronic lock, or a combination thereof. For example, a person authorized to insert medications directly into the apparatus and/or remove a replaceable cartridge 114 may be required to enter a code, provide a finger print, and/or use a key to access the opening 122 to remove or insert the medication and/or the replaceable cartridge 114. Any biometric identifier may be used. For example, in some instances, the locking mechanism 124 may comprise voice or face recognition software. That is, a person authorized to insert and/or remove the replaceable cartridge 114 may interact with a communication interface 108 and/or the user device 120 in order to unlock the locking mechanism 124. Other locking mechanisms 124 may also be used to prevent tampering with the opening 122.

In certain embodiments, the replaceable cartridge 114 may comprise a cartridge with multiple compartments 126 to hold predefined amounts of the prescribed substance. For example, in some instances, the replaceable cartridge 114 may be arranged in a cassette-like configuration as discussed below. In other instances, the cartridge may comprise a typical pill bottle. The prescribed substances may be the same or different. In some instances, the prescribed substance may be an opioid drug or the like, for which it is desirable to prevent abuse, misuse, or diversion to others than the prescribed patient. For example, the prescribed substance may include one or more solid drug units, such as tablets, capsules, or pills. In this manner, the replaceable cartridge 114 may be generally tamper-proof and only accessible by authorized personnel upon verification thereof. For example, a locking mechanism (similar to the locking mechanism 124) may be associated with the replaceable cartridge 114 to prevent access to someone other than a securely identified intended user.

The portable cartridge, container, bottle, and/or dispensing mechanism may be configured to accurately meter correct dosage. In some instances, the containers may comprise various sizes (i.e., 30, 60, 90, 120, 180 size containers), in which the control unit and dispensing mechanism are of the same size, and the bottles have universal size tops and bottoms, but with different capacities.

The replaceable cartridge 114 may be operable to dispense a predefined amount of a prescribed substance at a given time and/or date to a securely identified intended user. For example, the replaceable cartridge 114 may cooperate with the portable housing 102 to enable a patient to access a predefined amount of a prescribed substance at a given time and/or date to a securely identified intended user. As depicted in FIG. 1, the replaceable cartridge 114 may be wheel-shaped. In other embodiments, the replaceable cartridge 114 may be an elongated member. In some instances, the replaceable cartridge 114 may be arranged in a cassette-like configuration as discussed below. The replaceable cartridge 114, however, may be any shape. In one example, the replaceable cartridge 114 may be a replaceable cartridge with one or more prescribed substances within respective compartments 126. The dispensing mechanisms for releasing a dose of drug from the pill dispensing device 100 may reside wholly or partially in the replaceable cartridge 114, the housing 102, or a combination thereof. For example, the dispensing mechanism may be arranged in a cassette-like configuration, a rotational pill exchange, or the like.

In certain embodiments, the replaceable cartridge 114 may include a memory 128 in communication with a processor 130 (or a controller). In other embodiments, the cartridge may not include any electronic components. The memory 128 and the processor 130 of the replaceable cartridge 114 may be in communication with the memory 104 and the processor 106 of the portable housing 102. That is, the replaceable cartridge 114 and the portable housing 102 may cooperatively function to securely dispensing one or more prescribed substances at a given time and/or date to a securely identified intended user. In another embodiment, the memory 128 and the processor 130 of the replaceable cartridge 114 may be in communication with a processor associated with a server, authorized user system 118, and/or user device 120 via one or more networks 116. In any instance, the processors and/or the memories may include computer-executable instructions to operate the power source 110 to manipulate the replaceable cartridge 114 at the given time and/or date or on demand. For example, the replaceable cartridge 114 may provide a predefined amount of a prescribed substance to an access port 132 within the portable housing 102 that is generally tamperproof and accessible by a securely identified intended user.

In certain embodiments, authorized personnel, such as a physician or a pharmacist, may insert the replaceable cartridge 114 into the portable housing 102. In some instances, the replaceable cartridge 114 may be readymade. That is, the replaceable cartridge 114 may be prefilled with prescribed substances from the manufacturer, such as at a pharmacy or prescribed substance manufacturer. In other instances, the authorized personnel may prepare the replaceable cartridge 114 (such as a pill bottle) for insertion into the portable housing 102. That is, the authorized personnel may provide a predefined amount of prescribed substance in the compartments 126 of the replaceable cartridge 114. The replaceable cartridge 114 may be hand loaded and/or configured to be filled by way of an automated process (e.g., loading machine filled).

In certain embodiments, the authorized personnel may program or encode the processor 130 and/or memory 128 associated with the replaceable cartridge 114 to communicate with the portable housing 102 to provide the patient with a predefined amount of a prescribed substance at a given time and/or date. For example, the replaceable cartridge 114 may provide a predefined amount of a prescribed substance to the access port 132 within the portable housing 102 that is accessible by the patient at the given time and/or date based at least in part on one or more instructions provided by the authorized personnel. In other embodiments, prescription information and/or patient information can be programmed or encoded in the processor 130 and/or memory 128 associated with the replaceable cartridge 114, wherein some or all of the information can be utilized by the portable housing 102 to provide the patient with a predefined amount of a prescribed substance at a given time and/or date or on demand based on verification of the patient's identity.

In some instances, the replaceable cartridge 114 and/or the portable housing 102 may include identifier information. The identifier information may include, but is not limited to, medication information, dosage information, patient information, prescriber information, usage restrictions, time stamps, etc. The identifier information may be used to determine a chain of command regarding the handling of the prescribed substance and/or the dispensing of the prescribed substance.

As noted above, the prescribed substance may include an opioid drug or the like, for which it is desirable to prevent abuse, misuse, or diversion to others than the prescribed patient. Accordingly, it may be beneficial to provide information regarding the handling and/or the dispensing of the prescribed substance. For example, in some instances, the processors and/or the memories associated with the portable housing 102 and/or the replaceable cartridge 114 may be programmed to include the identifier information. In other instances, a bar code, QR code, RFID, label, or other readable medium comprising the identifier information may be associated with the replaceable cartridge 114 and/or the portable housing 102. The identifier information may be stored in a database, such as database 119 or the like.

In other embodiments, as noted above, all of the functionality described herein may be performed without a replaceable cartridge 114. That is, the pill dispensing device 100 may be operable to dispense a predefined amount of a prescribed substance at a given time and/or date or on demand to a securely identified intended user. For example, the pill dispensing device 100 may enable a patient to access a predefined amount of a prescribed substance at a given time and/or date. In some instances, the authorized personnel may provide a predefined amount of prescribed substance in the pill dispensing device 100. The pill dispensing device 100 may be hand loaded and/or configured to be filled by way of an automated process (e.g., loading machine filled).

Figure 5:
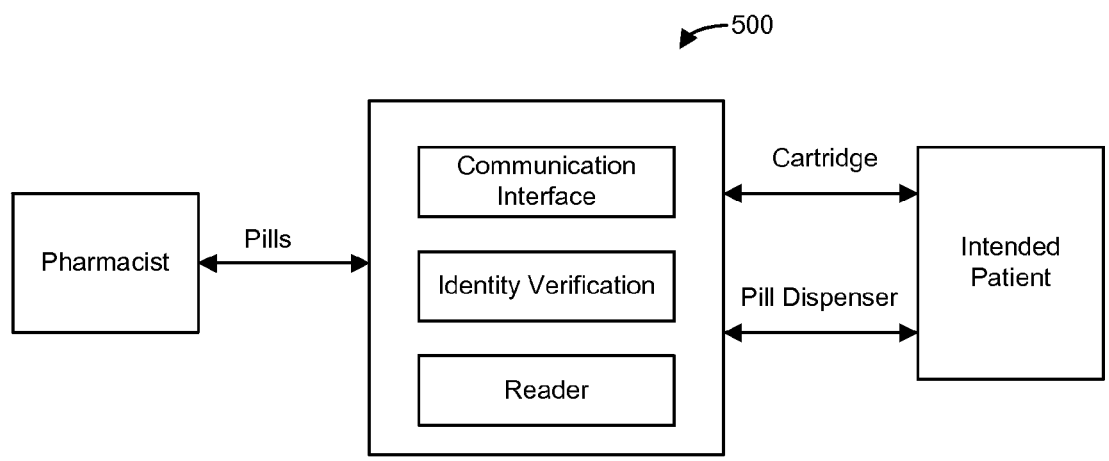
FIG. 5 schematically depicts an example system and apparatus for securely dispensing one or more prescribed substances at a given time and/or date in accordance with one or more embodiments of the disclosure.

In other embodiments, the pill dispensing device 100 may be loaded with medication and encrypted to the user and the contents through a docking station into which the pill dispensing device 100 is inserted, and into which both medications are inserted and identity encryption takes place. The loading device may load one or more pills per cartridge compartment and/or bulk load the housing, depending on the embodiment. For example, as depicted in FIG. 5, a loading or docking device 500 may be provided to receive a replaceable cartridge 114. The loading device 500 may be configured to insert a prescribed substance, such as pills, into the replaceable cartridge 114 and/or into the pill dispensing device 100 without a cartridge. The loading device 500 may be operated by a pharmacist or other personnel responsible for distributing a prescribed substance or otherwise loading a replaceable cartridge 114 or the pill dispensing device 100 with a prescribed substance.

The loading device 500 may include a reader and/or programming device to facilitate communication with the replaceable cartridge 114 and/or the pill dispensing device 100. The loading device 500 may include a communication interface so that the intended patient can view and/or confirm the information being encoded on the replaceable cartridge 114 and/or the pill dispensing device 100. Moreover, the loading device 500 may include an identification module configured to confirm the identity of the intended patient. For example, the verification module may include, but is not limited to, fingerprint identification, pin code encryption, face-recognition, voice-recognition, multi-source identification software, and the like. In this manner, the intended patient may insert the replaceable cartridge 114 and/or the pill dispensing device 100 into the loading device 500, and the intended patient may confirm their identity with the identity verification module. The pharmacist may insert pills into the loading device 500 opposite the intended patient. The replaceable cartridge 114 and/or the pill dispensing device 100 may be loaded with medication and encrypted with encryption information associated with the intended patient.

The remote monitoring component 112 may be configured to receive an indication when the pill dispensing device 100 is compromised. For example, one or more sensors may be associated with the anti-tampering aspects of the pill dispensing device 100. If the sensors indicate that the pill dispensing device 100 is being tampered with, the remote monitoring component 112 may send out a notification over the network 116. In addition, in certain embodiments, the remote monitoring component 112 may be configured to receive, by way of the network 116, an indication to dispense a prescribed substance at a time and/or date other than a programmed time and/or date. In some instances, an alert may be generated and transmitted by the processor and/or the remote monitoring component 112 if the prescribed substance is dispensed at a time and/or date other than a programmed time and/or date, or if the pill dispensing device 100 is compromised or opened, or if someone other than the intended patient accesses or attempts to access the prescribed substance. In other instances, an alert may be generated and transmitted over the network 116 by the processor and/or the remote monitoring component 112 indicating that the prescribed substance has been taken by the intended patient or someone else. In one example, if the pill dispensing device 100 is compromised or otherwise dispenses a prescribed substance at a time and/or date other than a programmed time and/or date, the prescribed substance may be rendered inert by the addition or release of a counter substance that may react with the prescribed substance to render it inert, inactive, or intolerable to one seeking to consume it. In another example, remote monitoring component 112 may monitor and/or transmit information regarding dispensing of the medication.

Figure 2:
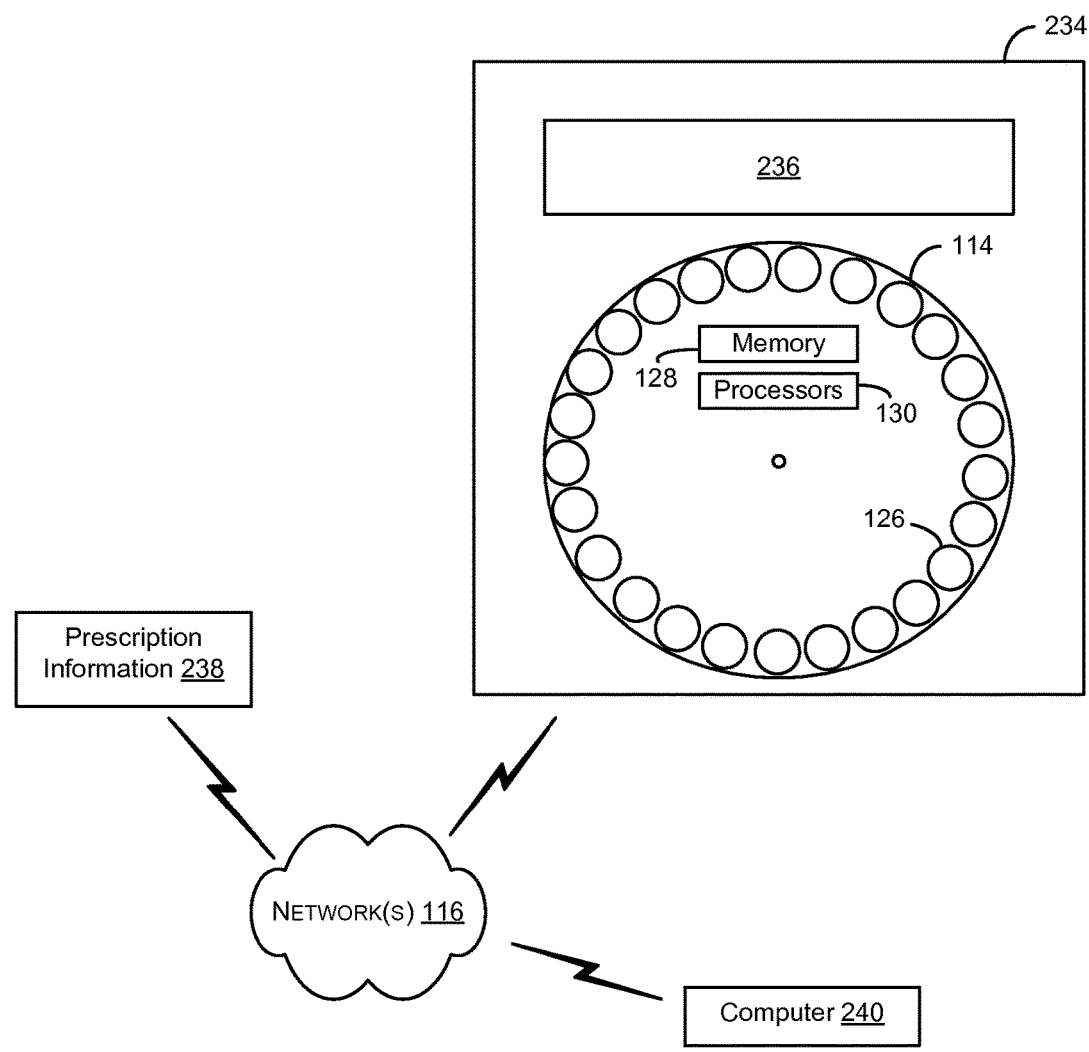
FIG. 2 schematically depicts an example system and apparatus for securely dispensing one or more prescribed substances at a given time and/or date in accordance with one or more embodiments of the disclosure.

FIG. 2 schematically depicts systems, methods, and apparatuses for loading a replaceable cartridge 114. In some instances, a loading device 234 may be provided to receive the replaceable cartridge 114 and to insert a prescribed substance or the like into the multiple compartments 126 of the replaceable cartridge 114. That is, the replaceable cartridge 114 may be inserted and/or removed (by hand or automated) from the loading device 234. The loading device 234 may be operated by authorized personnel, such as a physician or a pharmacist, responsible for distributing a prescribed substance or otherwise loading the replaceable cartridge 114 with a prescribed substance. The loading device 234 may include a reader and/or programming device 236 configured to facilitate communication with the replaceable cartridge 114. For example, the reader and/or programming device 236 may comprise one or more processor and/or memory configured to communication with the processor 130 and/or memory 128 of the replaceable cartridge 114.

In certain embodiments, prescription information 238 may be provided over the network 116 to the loading device 234. For example, when a paper and/or electronic prescription 238 is received, prescription information 238 may be transmitted or otherwise input to the loading device 234. The loading device 234 may transmit some or all of the prescription information 238 to the loading device 234. Prescription information 238 may include, but is not limited to, a name of a prescribed substance, a dosage regimen, a patient's contact information, a prescriber's contact information, etc. In this manner, the loading device 234 may be automated to load the replaceable cartridge 114 in accordance with the prescription information 238 received over the network 116 by the loading device. In some instances, the loading device 234 may be in communication with a computer 240 or the like to permit access to the prescription information 238 and/or to monitor, control, and/or otherwise communicate with the loading device 234.

Figure 6:
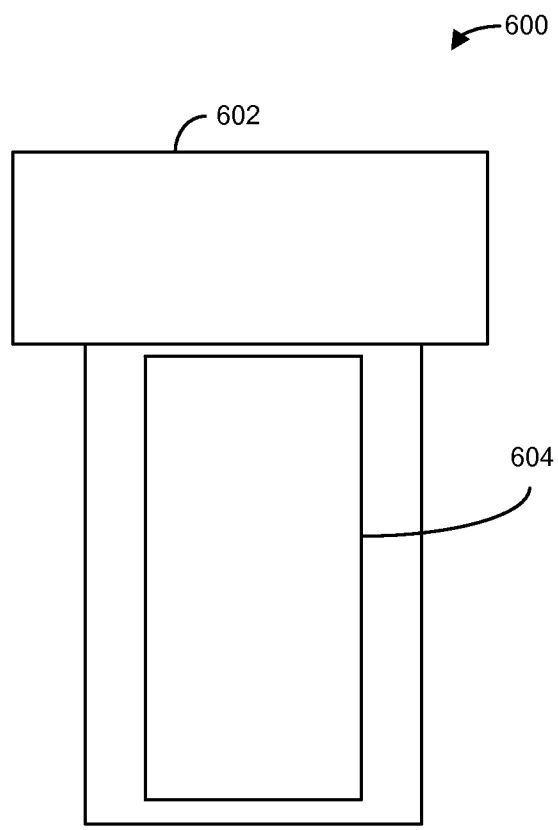
FIG. 6 schematically depicts an example system and apparatus for securely dispensing one or more prescribed substances at a given time and/or date in accordance with one or more embodiments of the disclosure.
Figure 11:
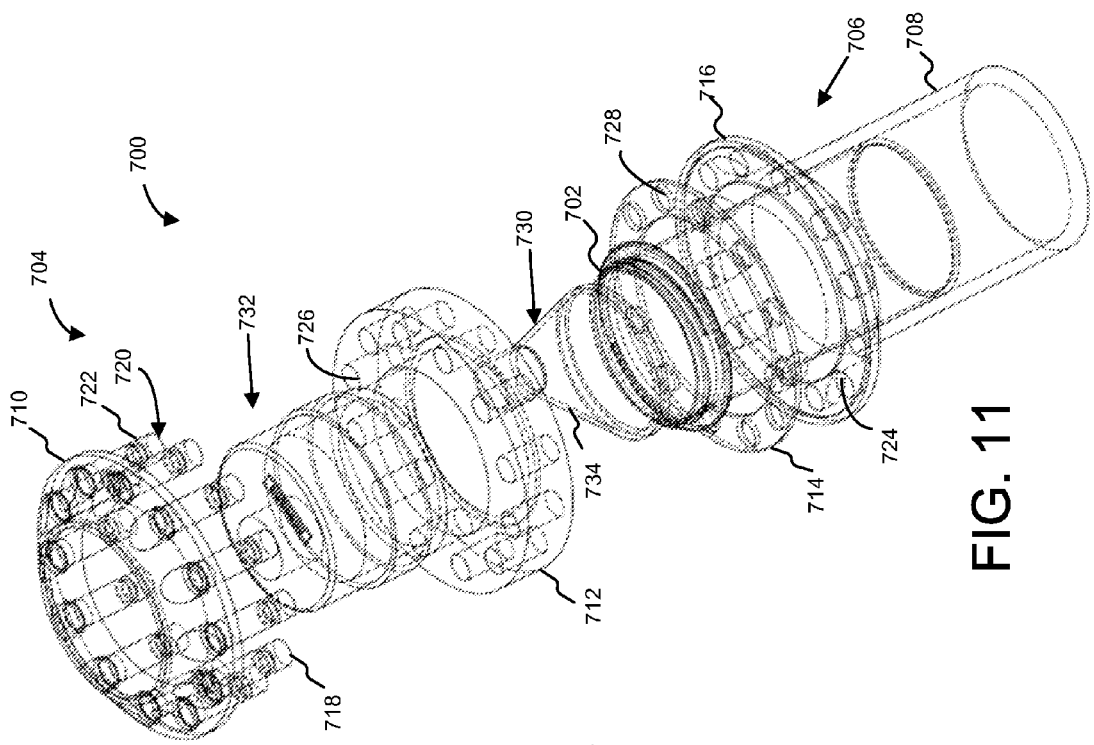
FIG. 11 depicts an example apparatus for securely dispensing one or more prescribed substances at a given time and/or date in accordance with one or more embodiments of the disclosure.

FIG. 6 depicts an alternate configuration of a pill dispensing device 600. For example, the pill dispensing device 600 may be configured to accept (or house) a bottle 604 of medication, such as a standard medicine bottle or the like. In this manner, the medicine bottle 604 (or container) may be secured within a tamper proof enclosure to prevent the bottle 604 from being compromised. The pill dispensing device 600 may include a smart capping/dispensing system 602 that regulates dispensing of the medication from the bottle 604. The smart cap 602 may include all of the tamper resistant functionality described above. For example, the intended user may have to provide identity verification, such as a finger print, pin code, etc. to access the medicine.

In some instances, the pill dispensing devices described herein may include a plunger type mechanism configured to dispense medication. For example, the plunger may move downward with each dosage. Moreover, the pill dispensing devices may include a metered gate for dispensing the medication. The pill dispensing device may include a camera, a display, an identification number, wireless functionality, a USB port or the like. In this manner, the pill dispensing device may be configured to be attached to a medication container or the like.

FIGS. 7-11 depict a pill dispensing device 700. In some instances, the pill dispensing device 700 may be configured to enclose (or surround) a bottle 702 of medication, such as a standard medicine bottle or the like. In this manner, the medicine bottle 702 (replaceable cartridge) may be secured within a tamper proof portable housing to prevent the bottle 702 from being compromised. For example, the pill dispensing device 700 may include a top portion 704 and a bottom portion 706 that collectively form a tamperproof portable housing about the bottle 702. In some instances, the top portion 704 may be mechanically secured (or locked) to the bottom portion 706 to prevent unauthorized access to the contents of the bottle 702.

In some instances, the bottom portion 706 may comprise a container 708 sized and shaped to receive the bottle 702 therein. That is, the bottle 702 may be at least partially positioned within the container 708. In certain embodiments, the container 708 may be transparent so that any labels on the bottle 702 may be visible from outside the container 708.

In some instances, the bottle 702 maybe omitted. For example, the prescribed substance (e.g., pills) may be stored directly in the container 708.

The pill dispensing device 700 may include a locking mechanism configured to secure the bottle 702 within the tamper proof enclosure to prevent the bottle 702 from being compromised. In an embodiment, the locking mechanism may include a top flange 710, a spacer 712, a locking ring 714, and a bottom flange 716. The top flange 710 may include a number of pins 718 extending therefrom. In some instances, an end 720 of the pins 718 may include a circumferential groove 722.

The bottom flange 716 may be disposed about the container 708. The bottom flange 716 may include a number of bores 724 configured to receive the ends 720 of the pins 718. That is, the bores 724 in the bottom flange 716 may correspond to the pins 718 extending from the top flange 710. In addition, the spacer 712 may include a number of passages 726 that correspond to the pins 718 extending from the top flange 710. Accordingly, the pins 718 may pass through the passages 726 in the spacer 712. Moreover, the locking ring 714 may include a number of openings 728 that correspond to the pins 718 extending from the top flange 710. The pins 718 may pass through the openings 728 in the locking ring 714.

When assembled, the top portion 704 and the bottom portion 706 may be locked together with the bottle 702 therein to form a portable housing enclosure. In other instances, the bottle 702 may be omitted, and the top portion 704 and the bottom portion 706 may be locked together with the prescribed substance disposed directly in the container 708.

To lock the top portion 704 to the bottom portion 706, the pins 718 extending from the top flange 710 may pass through the passages 726 in the spacer 712, through the openings 728 in the locking ring 714, and into the bores 724 of the bottom flange 716. When assembled in this manner, the circumferential grooves 722 disposed about the ends 720 of the pins 718 may be aligned with the locking ring 714. The locking ring 714 may be rotated slightly so that a portion of the locking ring 714 extends into the circumferential grooves 722 in the pins 718. This may prevent movement of the pins 718, thereby locking the top portion 704 to the bottom portion together 706. The locking ring 714 may be held in place by any means known in the art, such as a radial ratchet-type lock, spring mechanism, or the like.

The pill dispensing device 700 may include a dispensing mechanism. The dispensing mechanism may include a pill separation cone 730 and a dispensing housing 732. The pill separation cone 730 may have a conical portion 734 and tubular portion 736. The conical portion 734 may be disposed about the bottle 702 (or the container 708 if the bottle 702 is omitted). The conical portion 734 may be configured to funnel pills (or other prescribed substances) to the tubular portion 736 from the bottle 702 (or container 708). In some instances, the tubular portion 736 may be sized to receive one pill at a time from the conical portion 734.

The dispensing housing 732 may include one or more electrical components, a verification chamber 738, and an opening 740 for dispensing a pill. In some instances, the tubular portion 736 may dispense a pill into the verification chamber 738. The tubular portion 736 may dispense a single pill into the verification chamber 738 or multiple pills into the verification chamber 738. The verification chamber 738 may include one or more sensors, such as infrared sensors, electromagnetic sensors, weight sensors, cameras, etc. Any device capable of sensing the presence of a prescribed substance within the verification chamber 738 may be used.

Figure 10:
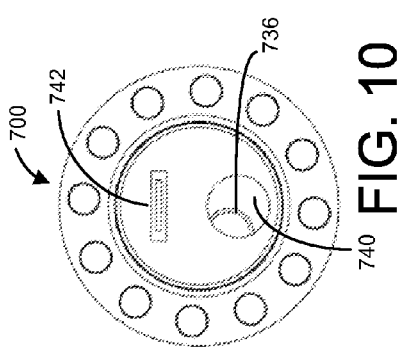
FIG. 10 depicts an example apparatus for securely dispensing one or more prescribed substances at a given time and/or date in accordance with one or more embodiments of the disclosure.
Figure 7:
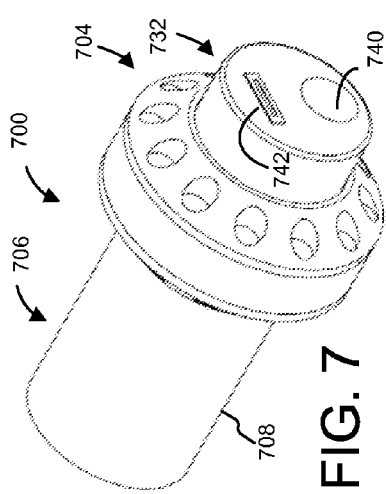
FIG. 7 depicts an example apparatus for securely dispensing one or more prescribed substances at a given time and/or date in accordance with one or more embodiments of the disclosure.
Figure 8:
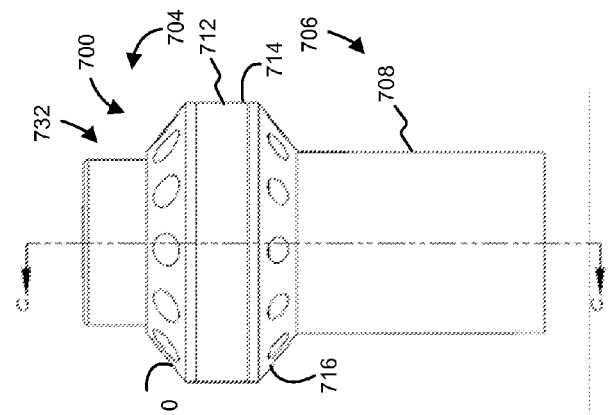
FIG. 8 depicts an example apparatus for securely dispensing one or more prescribed substances at a given time and/or date in accordance with one or more embodiments of the disclosure.
Figure 9:
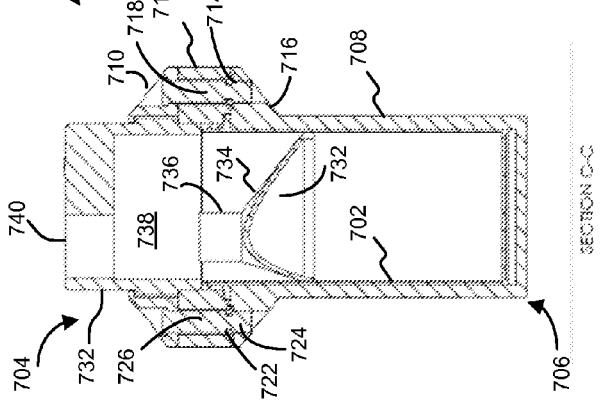
FIG. 9 depicts an example apparatus for securely dispensing one or more prescribed substances at a given time and/or date in accordance with one or more embodiments of the disclosure.

As noted above, the dispensing housing 732 may include an opening 740 for dispensing a pill. In this manner, after a pill passes through the verification chamber 738, it may be dispensed to a verified user by way of the opening 740. In certain embodiments, the opening 740, verification chamber 738, and the tubular portion 736 may be aligned such that a pill may be dispensed from the bottle 702 (or container 708). If the opening 740, verification chamber 738, and the tubular portion 736 are not aligned, pills may not be dispensed. For example, the one or more electrical components within the dispensing housing 732 may include an actuator or the like configured to control the position of the pill separation cone 730. The actuator may move (or rotate) the pill separation cone 730 to enable the dispensing of pills or to prevent the dispensing of pills. In another embodiment, the actuator may move the dispensing housing 732 about the pill separation cone 730, which may be stationary. For example, FIG. 9 depicts the opening 740, the verification chamber 738, and the tubular portion 736 lined up such that a pill may be dispensed. In contrast, FIG. 10 depicts the opening 740, the verification chamber 738, and the tubular portion 736 offset from one another such that a pill will not be dispensed. The actuator may be in communication with a controller. The controller may be configured to activate the actuator as described above.

The pill dispensing device 700 may include all of the tamper resistant functionality described in the disclosure, including those described with reference to FIG. 1. For example, the intended user may have to provide identity verification, such as a finger print, pin code, etc. to access the medicine. In some instances, a biometric identifier 742 may be disposed about the dispensing housing 732. The biometric identifier 742 may verify the identity of a user and instruct the controller to dispense one or more pills. Moreover, the pill dispensing device 700 may include a processor, a communication interface, a power source (e.g., a battery), and/or a remote monitoring component. In this manner, the pill dispensing device 700 may be in communication with other devices over a network or the like. In some instances, the pill dispensing device 700 may notify a third party over the network the rate of pills being dispensed or if the pill dispensing device 700 has been tampered with. In some instances, the pill dispensing device 700 may be programmed to dispense a pill on a dosage schedule. For example, the pill dispensing device 700 may only enable a verified user to receive a pill during a specified time frame.

Figure 12:
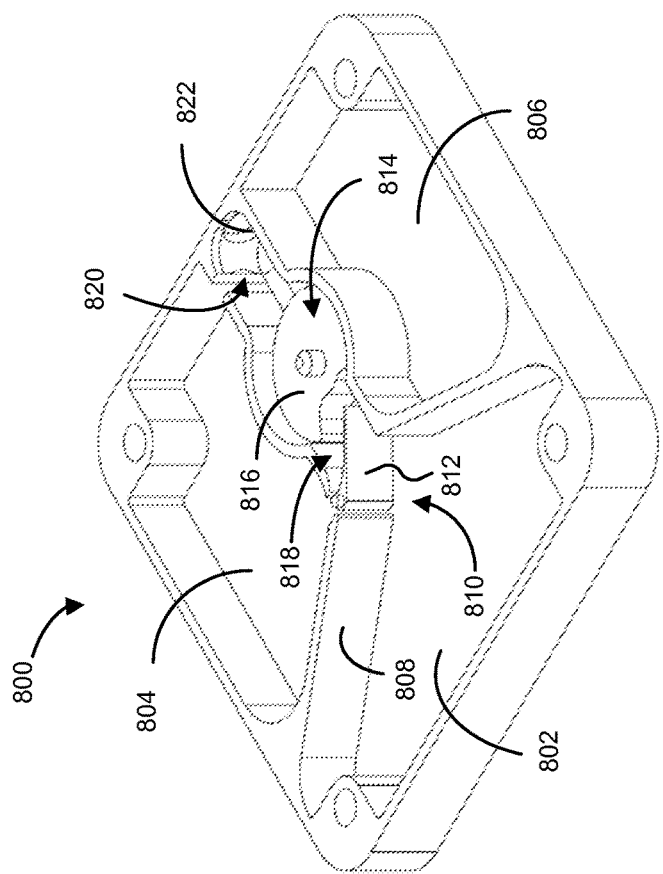
FIG. 12 depicts an example apparatus for securely dispensing one or more prescribed substances at a given time and/or date in accordance with one or more embodiments of the disclosure.
Figure 13:
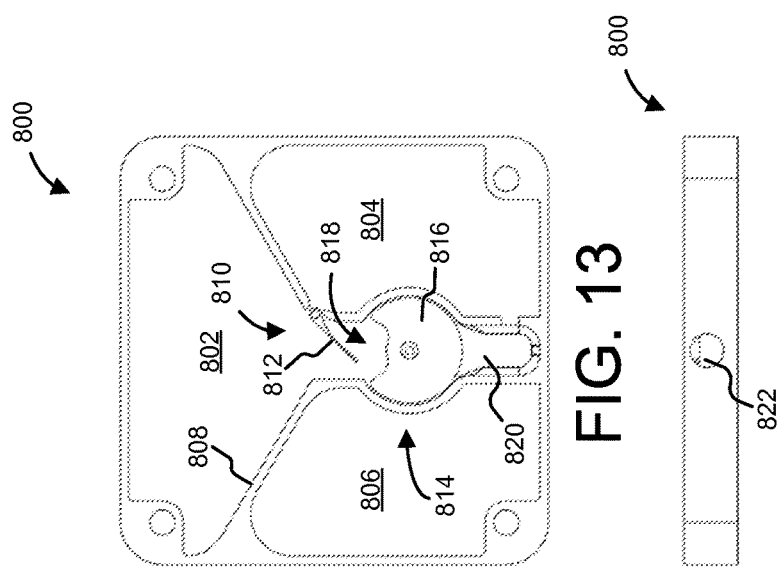
FIG. 13 depicts an example apparatus for securely dispensing one or more prescribed substances at a given time and/or date in accordance with one or more embodiments of the disclosure.
Figure 14:
FIG. 14 depicts an example apparatus for securely dispensing one or more prescribed substances at a given time and/or date in accordance with one or more embodiments of the disclosure.

FIGS. 12-14 depict a pill dispensing device 800. The pill dispensing device 800 is depicted with a side panel removed for clarity. The pill dispensing device 800 may include a portable housing having a pill storage area 802, a drive mechanism area 804, and an electronic components area 806. The pill storage area 802 may be configured to house one or more pills (or other prescribed substances) therein. The drive mechanism area 804 may be configured to house one or more actuators or the like therein. The electronic components area 806 may be configured to house one or more electronics therein, such as a processor, a communication interface, a power source (e.g., a battery), and/or a remote monitoring component.

The pill storage area 802 may include a funnel-like shape 808 for directing one or more pills towards a ratchet assembly 810. In some instances, the pill storage area 802 may include a plunger-like device or spring loaded device for urging the pills towards the ratchet assembly 810.

The ratchet assembly 810 may include a moveable arm 812. The moveable arm 812 may be in communication with an actuator or the like for adjusting the position of the movable arm 812. The moveable arm 812 may be adjusted to enable one or more pills to pass from the pill storage area 802 to a rotational pill exchange assembly 814. For example, the moveable arm 812 may be adjusted to enable multiple pills to pass to the rotational pill exchange assembly 814, or the moveable arm 812 may be adjusted to limit a one pill at a time to pass to the rotational pill exchange assembly 814.

The rotational pill exchange assembly 814 may include a rotatable wheel 816. The rotatable wheel 816 may include a cutout 818. The cutout 818 may be configured to receive one or more pills from the ratchet assembly 810. For example, as the rotatable wheel 816 rotates, the cutout 818 may pass by the ratchet assembly 810. Each time the cutout 818 passes the ratchet assembly 810, it may receive one or more pills from the ratchet assembly 810. The cutout 818 may rotate from the ratchet assembly 810 to a validation port 820, where the pills may be transferred. That is, the cutout 818 may be configured to transfer one or more pills between the ratchet assembly 810 and the validation port 820 as the rotatable wheels 816 rotates.

In some instances, the rotational pill exchange assembly 814 may include one or more sensors. For example, the sensors may detect the presence of one or more pills in the cutout 818 before and after the validation port 820. In this manner, the sensors may be configured to determine if a pill was transferred from the cutout 818 to the validation port 820. Similarly, the validation port 820 may include one or more sensors. The sensors in the validation port 820 may be configured to sense the presence of one or more pills in the validation port 820.

The validation port 820 may be in communication with an opening 822 for dispensing one or more pills. The pill dispensing device 800 may include all of the tamper resistant functionality described in the disclosure, including those described with reference to FIG. 1. For example, the intended user may have to provide identity verification, such as a finger print, pin code, etc. to access the medicine. Once the user is verified, a controller or the like may instruct the ratchet assembly and/or the rotational pill exchange assembly to dispense one or more pills. Moreover, the pill dispensing device 800 may be in communication with other devices over a network or the like. In some instances, the pill dispensing device 800 may notify a third party over the network the rate of pills being dispensed or if the pill dispensing device 800 has been tampered with. In some instances, the pill dispensing device 800 may be programmed to dispense a pill on a dosage schedule. For example, the pill dispensing device 800 may only enable a verified user to receive a pill during a specified time frame.

Figure 15:
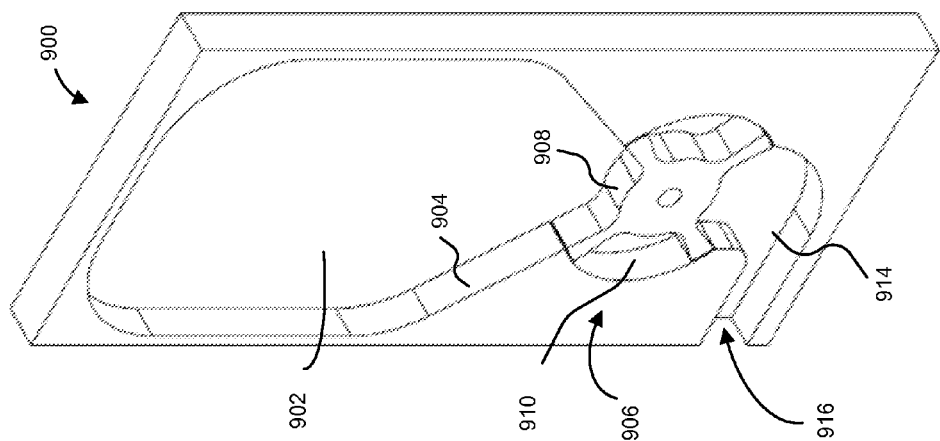
FIG. 15 depicts an example apparatus for securely dispensing one or more prescribed substances at a given time and/or date in accordance with one or more embodiments of the disclosure.
Figure 16:
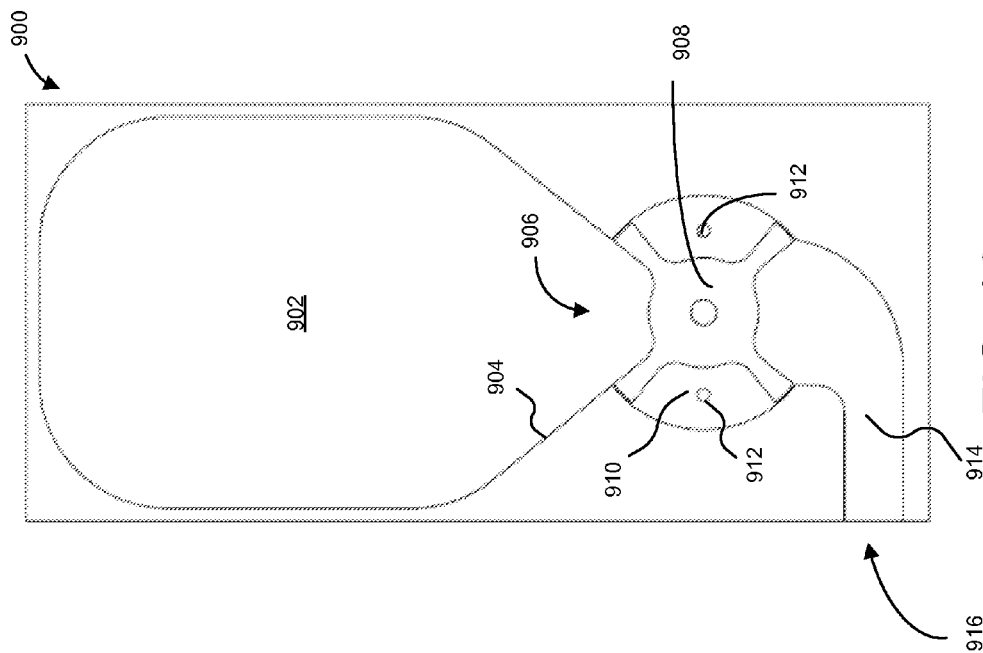
FIG. 16 depicts an example apparatus for securely dispensing one or more prescribed substances at a given time and/or date in accordance with one or more embodiments of the disclosure.

FIGS. 15 and 16 depict a pill dispensing device 900 comprising a portable housing. The pill dispensing device 900 may include a pill storage area 902. The pill dispensing device 900 also may include one or more electronics, such as a processor, one or more actuators, a communication interface, a power source (e.g., a battery), and/or a remote monitoring component.

The pill storage area 902 may include a funnel-like shape 904 for directing one or more pills towards a rotational pill exchange assembly 906. In some instances, the pill storage area 902 may include a plunger-like device or spring loaded device for urging the pills towards the rotational pill exchange assembly 906.

The rotational pill exchange assembly 906 may include a rotatable wheel 908. The rotatable wheel 908 may include one or more cutouts 910. In other instances, the rotatable wheel 908 may include a single cutout similar to the cutout 818 described above. The cutouts 910 may be configured to receive one or more pills from the pill storage area 902. For example, as the rotatable wheel 908 rotates, the cutouts 910 may pass by the pill storage area 902. Each time the cutouts 910 pass the pill storage area 902, they may receive one or more pills from the pill storage area 902. The cutouts 910 may rotate from the pill storage area 902 to a channel 914, where the pills may be transferred. That is, the cutouts 910 may be configured to transfer one or more pills between the pill storage are 902 and the channel 914 as the rotatable wheels 908 rotates.

In some instances, the rotational pill exchange assembly 906 may include one or more sensors 912. For example, the sensors 912 may detect the presence of one or more pills in the cutouts 910 before and after each cutout passes the channel 914. In this manner, the sensors 912 may be configured to determine if a pill was transferred from the cutouts 910 to the channel 914. In one example, the sensors 912 may detect the presence of one or more pills within the cutouts 910 before the channel 914. Moreover, the sensors 912 may detect the absence of one or more pills within the cutouts 910 after the channel 914, which may indicate the pills were dispensed.

The channel 914 may be in communication with an opening 916 for dispensing one or more pills. In some instances, the channel 914 may be curved to prevent tampering with the device. The pill dispensing device 900 may be similar to the pill dispensing device 800. That is, the various components of the pill dispensing device 800 may be included or omitted from the pill dispensing device 900 and vice versa. For example, the ratchet assembly described above may be incorporated into the pill dispensing device 900.

The pill dispensing device 900 may include all of the tamper resistant functionality described in the disclosure, including those described with reference to in FIG. 1. For example, the intended user may have to provide identity verification, such as a finger print, pin code, etc. to access the medicine. Once the user is verified, a controller or the like may instruct the rotational pill exchange assembly to dispense one or more pills. Moreover, the pill dispensing device 900 may be in communication with other devices over a network or the like. In some instances, the pill dispensing device 900 may notify a third party over the network the rate of pills being dispensed or if the pill dispensing device 900 has been tampered with. In some instances, the pill dispensing device 900 may be programmed to dispense a pill on a dosage schedule. For example, the pill dispensing device 900 may only enable a verified user to receive a pill during a specified time frame.

Figure 17:
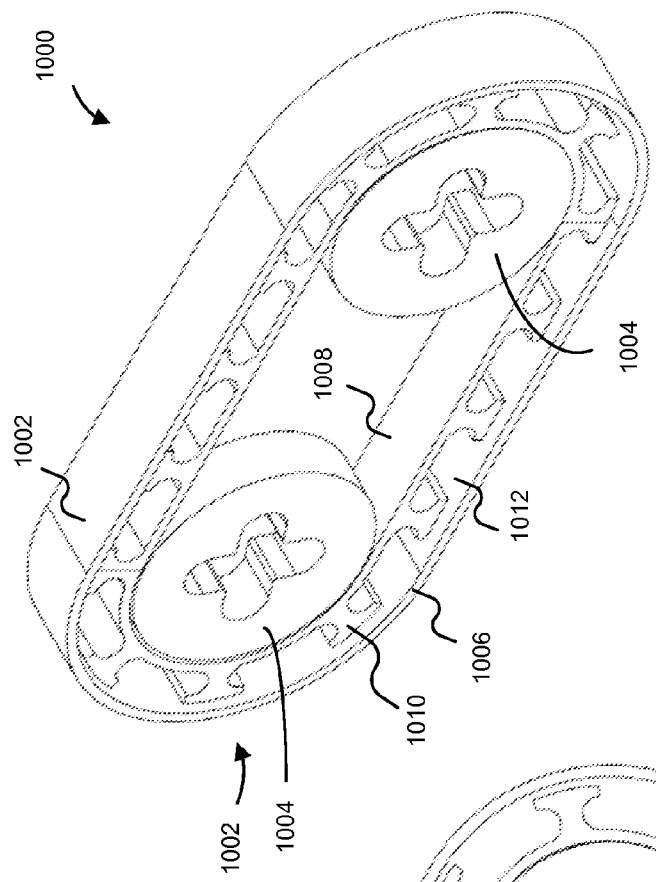
FIG. 17 depicts an example apparatus for securely dispensing one or more prescribed substances at a given time and/or date in accordance with one or more embodiments of the disclosure.
Figure 18:
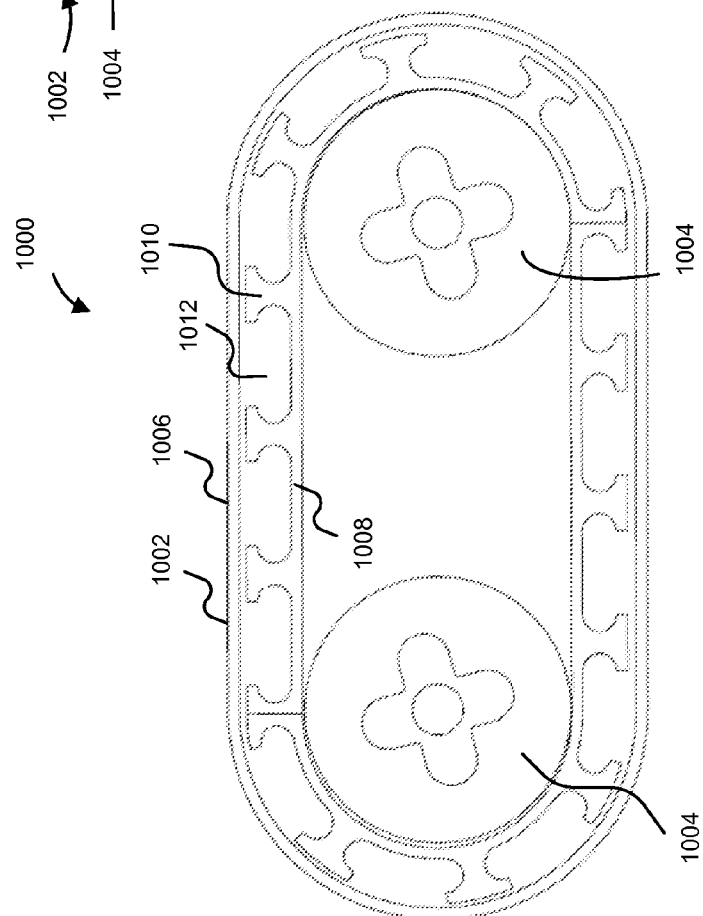
FIG. 18 depicts an example apparatus for securely dispensing one or more prescribed substances at a given time and/or date in accordance with one or more embodiments of the disclosure.

FIGS. 17 and 18 depict a cassette-like mechanism 1000 for dispensing one or more pills (or other prescribed substances) securely. The cassette-like mechanism 1000 may be used in any of the embodiments described herein. For example, the cassette-like mechanism 1000 may be used to dispense one or more pills from a tamperproof portable housing. The tamperproof portable housing may include all of the functionality described in the disclosure, including those described with reference to FIG. 1.

In certain embodiments, the cassette-like mechanism 1000 may include a continuous track 1002 disposed about two or more wheels 1004. The continuous track 1002 may include an outer track 1006 and an inner track 1008. In some instances, the outer track 1006 may be stationary, and the inner track 1008 may rotate about the wheels 1004. In other instances, both the inner track 1008 and the outer track 1006 may rotate about the wheels 1004. A number of spacers 1010 may extend between the inner track 1008 and the outer track 1006. A number of chambers 1012 may be defined between adjacent spacers 1010. Each chamber 1012 may be configured to house one or more pills therein. As the inner track 1008 rotates about the wheels 1004, the chambers 1012 may rotate as well. In this manner, the chambers 1012 may move the pills along the continuous track's path. In some instances, the portable housing may include an opening. As the chambers 1012 rotate past the opening, the pills may be accessible from outside the enclosure. The cassette-like mechanism 1000 may be incorporated into any of the embodiments discussed in the disclosure.

Illustrative Methods

Figure 3:
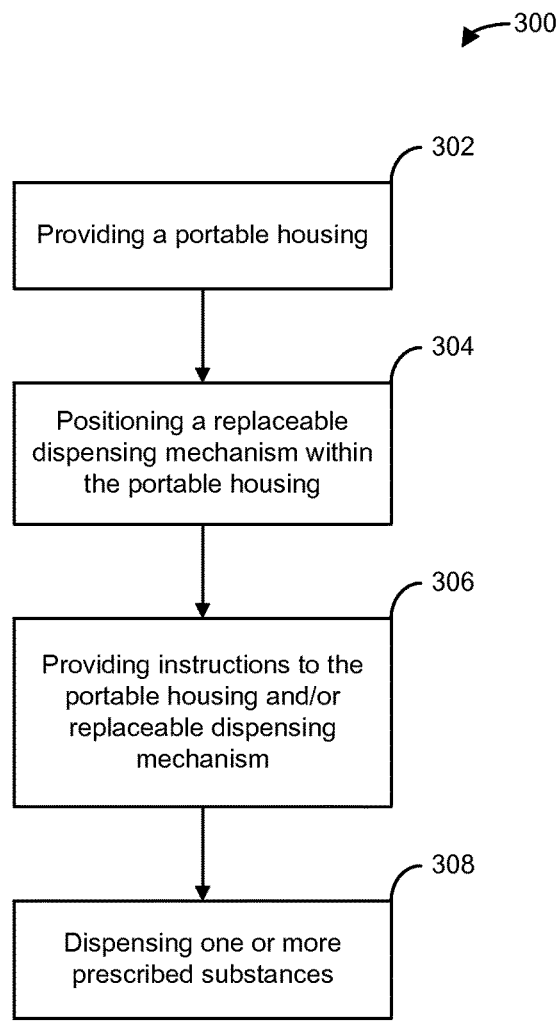
FIG. 3 is a flow diagram depicting an illustrative method for securely dispensing one or more prescribed substances at a given time and/or date in accordance with one or more embodiments of the disclosure.

FIG. 3 is a flow diagram depicting an illustrative method 300 for securely dispensing one or more prescribed substances at a given time and/or date in accordance with one or more embodiments of the disclosure.

At block 302 of method 300, a portable housing 102 may be provided that is generally tamper-proof and may only be opened by authorized personnel, such as a physician or a pharmacist. In some instances, the portable housing 102 may be sized and shaped to be carried by a patient. For example, the portable housing 102 may be configured to be held in the hand of the patient and/or carried in the pocket of the patient. At block 304 of method 300, a replaceable cartridge 114 may be positioned within the portable housing 102. The replaceable cartridge 114 may comprise a removable cartridge with multiple compartments 126 or a single compartment configured to hold predefined amounts of the prescribed substance. The replaceable cartridge 114 may be generally tamper-proof and only accessible by authorized personnel upon verification thereof. The replaceable cartridge 114 may be operable to dispense a predefined amount of a prescribed substance at a given time and/or date or on demand. For example, the replaceable cartridge 114 may cooperate with the portable housing 102 to enable a patient to access a predefined amount of a prescribed substance at a given time and/or date.

At block 306 of method 300, the portable housing 102 and/or the replaceable cartridge 114 may be programmed to dispense the prescribed substance. That is, in certain embodiments, authorized personnel may program the processor 130 and/or memory 128 associated with the replaceable cartridge 114 to communicate with the processor 106 and/or the memory 104 associated with the portable housing 102 to provide the patient with a predefined amount of a prescribed substance at a given time and/or date. For example, the replaceable cartridge 114 may provide a predefined amount of a prescribed substance to the access port 132 within the portable housing 102 that is accessible by the patient at the given time and/or date based on the instructions provided by the authorized personnel. In some instances, an operator of the authorized user system 118 may remotely modify the programmed medication schedule of the pill dispensing device 100.

At block 308 of method 300, the pill dispensing device 100 may dispense one or more prescribed substances. For example, the pill dispensing device 100 may dispense one or more prescribed substances based on (1) programmed instructions in the memory and/or processors, (2) an authorization to dispense the prescribed substance received over the network 116, and/or (3) upon verification of the patient, etc. The steps described in blocks 302-308 of method 300 may be performed in any order. Moreover, certain steps may be omitted, while other steps may be added.

Figure 4:
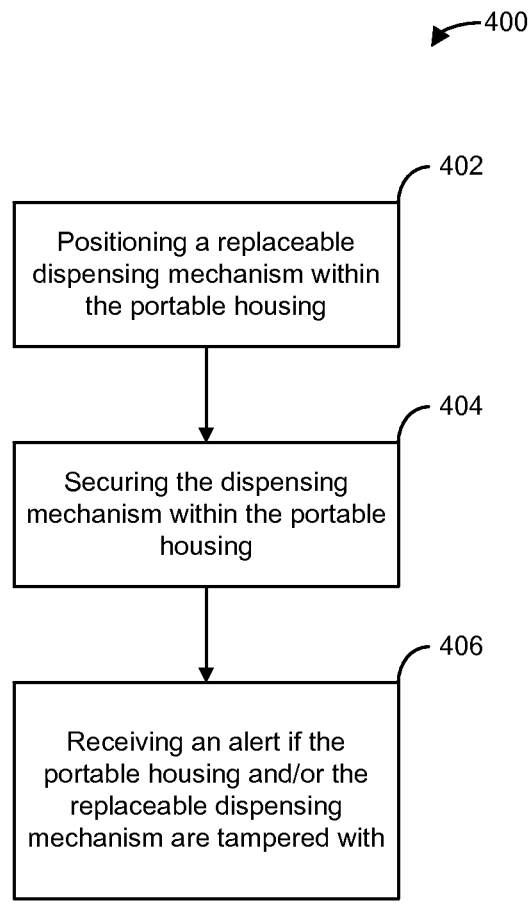
FIG. 4 is a flow diagram depicting an illustrative method for securely dispensing one or more prescribed substances at a given time and/or date in accordance with one or more embodiments of the disclosure.

FIG. 4 is a flow diagram depicting an illustrative method 400 for securely dispensing one or more prescribed substances at a given time and/or date in accordance with one or more embodiments of the disclosure.

At block 402 of method 400, the replaceable cartridge 114 may be positioned within the portable housing 102 by way of an opening 122. After positioning the replaceable cartridge 114 within the portable housing 102, the replaceable cartridge 114 may be secured within the portable housing 102 at block 404. For example, the opening 122 may include a locking mechanism 124 or the like. In some instances, the locking mechanism 124 may be a mechanical lock, a biometric lock, an electronic lock, or a combination thereof. For example, a person authorized to insert and/or remove the replaceable cartridge 114 may be required to enter a code, provide a finger print, and/or use a key to access the opening 122 to remove or insert the replaceable cartridge 114. Any biometric identifier may be used. For example, in some instances, the locking mechanism 124 may comprise voice recognition software. That is, a person authorized to insert and/or remove the replaceable cartridge 114 may speak into the communication interface 108 and/or the user device 120 in order to unlock the locking mechanism 124. Other locking mechanisms 124 may also be used to prevent tampering with the opening 122.

At block 406 of method 400, an alert may be generated and transmitted by the processor and/or the remote monitoring component 112 if the prescribed substance is dispensed at a time and/or date other than a programmed time and/or date, or if the portable housing 102 and/or replaceable cartridge 114 is compromised or opened, or if someone other than the patient accesses or attempts to access the prescribed substance. The steps described in blocks 402-406 of method 400 may be performed in any order. Moreover, certain steps may be omitted, while other steps may be added.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A system for dispensing a solid drug unit comprising a prescription medication to a patient, the system comprising:
    a portable pill dispensing device, comprising:
        a pill storage area configured to bulk store a plurality of the solid drug units therein,
        a locking mechanism configured to secure the plurality of the solid drug units within the portable pill dispensing device,
        an opening for dispensing the solid drug units from the portable pill dispensing device,
        a rotational pill exchange assembly disposed between the opening and the pill storage area, wherein the rotational pill dispensing exchange assembly comprises a rotatable wheel with a cutout sized and shaped to receive at least one of the solid drug units from the pill storage area, wherein rotation of the rotatable wheel moves the received at least one of the solid drug units from the pill storage area to the opening, and
        a moveable arm rotatably disposed between the pill storage area and the rotational pill exchange, wherein the moveable arm is configured to control passage of the solid drug units, one at a time, from the pill storage area to the rotational pill exchange assembly; and
    a handheld mobile device associated with the patient and in wireless communication with the portable pill dispensing device, wherein the handheld mobile device is configured to verify an identity of the patient in order for the patient to access the solid drug unit from the portable pill dispensing device,
    wherein the portable pill dispensing device is operable to dispense a predefined number of the solid drug units only at a specific time and date based on a prescribed dosage schedule.

2. The system of claim 1, wherein the prescribed medication comprises an opioid drug.

3. The system of claim 1, wherein the solid drug unit is a tablet or capsule.

4. The system of claim 1, wherein the portable pill dispensing device comprises at least one of a processor, a memory, a power source, a communication interface, or a remote monitoring component.

5. The system of claim 1, wherein the locking mechanism comprises a mechanical lock, a biometric lock, an electronic lock, voice activated lock, or a combination thereof.

6. The system of claim 1, wherein the portable pill dispensing device comprises an access port that is accessible by the patient once the identity of the patient is verified at the handheld mobile device based on instructions provided by an authorized personnel.

7. The system of claim 1, wherein the handheld mobile device is configured to transmit an alert to remind the patient to dispense and self-administer a dose of the prescribed medication, or to provide the patient with medication instructions.

8. The system of claim 1, wherein the handheld mobile device must be within a certain proximity of the portable pill dispensing device in order for the pill dispensing device to dispense the prescribed medication.

9. The system of claim 1, wherein the portable pill dispenser comprises a remote monitoring component in wireless communication with an authorized user system over a network.

10. The system of claim 9, wherein the authorized user system dynamically adjusts the prescribed dosage schedule based on feedback from the portable pill dispensing device.

11. The system of claim 9, wherein the authorized user system is alerted if someone other than the patient attempts to access the prescribed medication.

12. The system of claim 1, wherein the identity of the patient is verified by the patient entering a code into the handheld mobile device, answering a question on the handheld mobile device, activating an identity encryption sequence on the handheld mobile device, providing biometric recognition on the handheld mobile device, speaking into the handheld mobile device, or a combination thereof.

13. The system of claim 1, wherein the pill storage area comprises a funnel, and wherein the moveable arm is rotatably attached to an end of the funnel between the pill storage area and the rotational pill exchange.

14. A method for securely dispensing a drug to a patient, comprising:
providing a plurality of units of the drug within a portable pill dispensing device, wherein portable pill dispensing device, comprises:
a pill storage area configured to bulk store the plurality of units of the drug therein,
a locking mechanism configured to secure the plurality of units of the drug within the portable pill dispensing device,
an opening for dispensing the plurality of units of the drug from the portable pill dispensing device,
a rotational pill exchange assembly disposed between the opening and the pill storage area, wherein the rotational pill dispensing exchange assembly comprises a rotatable wheel with a cutout sized and shaped to receive at least one of the plurality of units of the drug from the pill storage area, and
a moveable arm rotatably disposed between the pill storage area and the rotational pill exchange, wherein the moveable arm is configured to move at least one of the plurality of units of the drug from the pill storage area to the rotational pill exchange assembly; and
securing the plurality of units of the drug within the portable pill dispensing device;
verifying an identity of the patient at a handheld mobile device associated with the patient and in wireless communication with the portable pill dispensing device in order for the patient to access at least one of the plurality of units of the drug from the portable pill dispensing device;
dispensing at least one of the plurality of units of the drug from the portable pill dispensing device at a specific time and date based on a predefined dosage schedule;
receiving an alert at an authorized user system in wireless communication with the portable pill dispensing device over a network if at least one of the plurality of units of the drug is dispensed at a time and/or date other than at the predefined dosing schedule; and
dynamically controlling the dosage schedule by the authorized user system based on feedback from the portable pill dispensing device.

15. The method of claim 14, wherein the authorized user system comprises a database.

16. The method of claim 14, wherein the portable housing comprises at least one of a processor, a memory, a power source, a communication interface, or a remote monitoring component.

17. A portable pill dispensing device for dispensing a solid drug unit comprising a prescribed medication to a patient, the device comprising:
a pill storage area configured to bulk store a plurality of the solid drug units therein;
an opening for dispensing the solid drug units from the portable pill dispensing device;
a rotational pill exchange assembly disposed between the opening and the pill storage area, wherein the rotational pill dispensing exchange assembly comprises a rotatable wheel with a cutout sized and shaped to receive at least one of the solid drug units from the pill storage area; and
a moveable arm disposed between the pill storage area and the rotational pill exchange, wherein the moveable arm is configured to permit the solid drug units to pass one at a time from the pill storage area to the rotational pill exchange assembly,
wherein the storage area comprises a funnel configured to direct the solid drug units to the rotational pill exchange assembly,
wherein the moveable arm is rotatably attached to an end of the funnel between the pill storage area and the rotational pill exchange, and
wherein the portable pill dispensing device is operable to dispense a predefined number of the solid drug units at a specific time and date based on a predefined dosage schedule.

18. The portable pill dispensing device of claim 17, further comprising a locking mechanism configured to secure the plurality of solid drug units within the portable dispensing device.

19. The portable pill dispensing device of claim 17, further comprising a controller configured to control rotation of the rotatable wheel to move one of the solid drug units, received from the pill storage area, to the opening.

* * * * *